US012773509B2

(12) United States Patent
Göbel

(10) Patent No.: US 12,773,509 B2
(45) Date of Patent: Oct. 27, 2026

(54) FLOW-OPTIMIZED SUPPLY TO A BALLOON ELEMENT THAT SEALS DYNAMICALLY AND IN SYNC WITH ORGANS

(71) Applicant: Advanced Medical Balloons GmbH, Waghäusel (DE)

(72) Inventor: Fred Göbel, Lützelbach (DE)

(73) Assignee: Advanced Medical Balloons GmbH, Waghäusel (DE)

( * ) Notice: Subject to any disclaimer, the term of this patent is extended or adjusted under 35 U.S.C. 154(b) by 1166 days.

(21) Appl. No.: 17/763,362

(22) PCT Filed: Sep. 24, 2020

(86) PCT No.: PCT/IB2020/058935
§ 371 (c)(1),
(2) Date: Mar. 24, 2022

(87) PCT Pub. No.: WO2021/059183
PCT Pub. Date: Apr. 1, 2021

(65) Prior Publication Data

US 2022/0347413 A1 Nov. 3, 2022

(30) Foreign Application Priority Data

Sep. 24, 2019 (DE) ..................... 10 2019 006 680.4

(51) Int. Cl.
*A61M 16/04* (2006.01)
*A61M 16/20* (2006.01)

(52) U.S. Cl.
CPC ...... *A61M 16/044* (2013.01); *A61M 16/0445* (2014.02); *A61M 16/047* (2013.01); *A61M 16/208* (2013.01); *A61M 2205/0294* (2013.01)

(58) Field of Classification Search
CPC .. A61M 16/00; A61M 16/04; A61M 16/0402; A61M 16/0434; A61M 16/044;
(Continued)

(56) References Cited

U.S. PATENT DOCUMENTS 3,707,151 A * 12/1972 Jackson ............ A61M 16/0452 128/207.15
3,794,043 A 2/1974 McGinnis
(Continued)

FOREIGN PATENT DOCUMENTS

DE 3028568 11/1982
WO WO 99/045991 9/1999
(Continued)

OTHER PUBLICATIONS

Badenhorst, C., Changes in Tracheal Cuff Pressure During Respiratory Support, Critical Care Medicine, 1987, vol. 15, No. 4, pp. 300-302.

(Continued)

*Primary Examiner* — Colin W Stuart
(74) *Attorney, Agent, or Firm* — McDonnell Boehnen Hulbert & Berghoff LLP

(57) ABSTRACT

The invention relates to a device for the dynamically adapting sealing of an organ or a body cavity, e.g. the windpipe (trachea) of an intubated and ventilated patient, wherein the sealing balloon element is produced via particularly rapid shifting of filling medium from an extracorporeal reservoir or an extracorporeal source to the sealing balloon, and wherein, in the dynamic sealing of the trachea according to the example case, a balloon-type foil body preferably formed with residual material in the diameter, i.e. exceeding the tracheal diameter, is in contact with the inner wall of the trachea in a sealing manner and with a pressure that is as constant as possible, wherein fluctuations in the balloon volume, caused by fluctuations in the intrathoracic pressure relating to the mechanics of breathing, are compensated as quickly as possible by supplying volume from an extracorporeal reservoir or an extracorporeal source, and the tracheal secretion sealing of the balloon is thereby kept continuous. This is both made possible by a sufficiently high-volume
(Continued)

supply of the balloon filling medium to the cuff, and also prevents steps, gaps or ridges in the supply system, whereby volume flow directed towards the balloon can be minimised, which is crucial for a rapid-as-possible stabilising of the filling volume in the balloon, in particular with small pressure differences between 15 and 30 mbar that are driving the volume flow.

31 Claims, 5 Drawing Sheets

(58) Field of Classification Search
CPC ............ A61M 16/045; A61M 16/0445; A61M 16/047
See application file for complete search history.

(56) References Cited

U.S. PATENT DOCUMENTS

| | | | | |
|---|---|---|---|---|
| 4,159,722 | A | 7/1979 | Walker | |
| 4,856,510 | A | 8/1989 | Kowalewski | |
| 5,235,973 | A | 8/1993 | Levinson | |
| 5,361,753 | A * | 11/1994 | Pothmann | A61M 16/021 128/207.15 |
| 6,526,977 | B1 * | 3/2003 | Gobel | A61M 16/0456 128/207.14 |
| 6,647,984 | B1 | 11/2003 | O'Dea | |
| 6,918,391 | B1 * | 7/2005 | Moore | A61M 16/0463 128/207.14 |
| 8,307,830 | B2 * | 11/2012 | Clayton | A61L 29/04 128/207.14 |
| 2014/0366874 | A1 * | 12/2014 | Deutsch | A61B 5/022 128/202.13 |
| 2015/0101598 | A1 * | 4/2015 | Wang | A61M 16/0459 128/202.16 |
| 2015/0283343 | A1 * | 10/2015 | Schnell | A61M 25/10184 128/207.15 |
| 2016/0038699 | A1 * | 2/2016 | Higashiyama | A61M 16/0003 128/207.15 |
| 2017/0007790 | A1 * | 1/2017 | Walker | A61M 16/0452 |
| 2019/0262562 | A1 | 8/2019 | Zachar et al. | |

FOREIGN PATENT DOCUMENTS

| | | |
|---|---|---|
| WO | WO 2013/139986 | 9/2013 |
| WO | WO 2014/090680 | 6/2014 |
| WO | WO 2016/087930 | 6/2016 |
| WO | WO 2017/085540 | 5/2017 |

OTHER PUBLICATIONS

Bassi, G. et al., An In Vitro Study to Assess Determinant Featurees Associated With Fluid Sealing in the Design of Endotracheal Tube Cuffs and Exerted Tracheal Pressures, Critical Care Medicine, 2013, vol. 41, Issue 2, pp. 518-526.

* cited by examiner

FLOW-OPTIMIZED SUPPLY TO A BALLOON ELEMENT THAT SEALS DYNAMICALLY AND IN SYNC WITH ORGANS

REFERENCE TO PENDING PRIOR PATENT APPLICATIONS

This patent application claims benefit of International (PCT) Patent Application No. PCT/IB2020/058935, filed 24 Sep. 2020 by Creative Balloons GmbH and Fred Göbel for FLOW-OPTIMISED SUPPLY TO A BALLOON ELEMENT THAT SEALS DYNAMICALLY AND IN SYNC WITH ORGANS, which patent application, in turn, claims benefit of German Patent Application No. DE 10 2019 006 680.4, filed 24 Sep. 2019.

The two (2) above-identified patent applications are hereby incorporated herein by reference.

FIELD OF THE INVENTION

The invention relates to devices for the dynamic occlusion, sealing and/or tamponade of a hollow organ, which is in sync with organs, by means of a balloon-type element, in particular to the dynamically adapting, aspiration-preventative secretion sealing of an intubated trachea in the case of independently breathing patients as well as in the case of patients who are being mechanically ventilated in a supporting spontaneous breathing mode. The invention relates in particular to a device for the dynamically adapting sealing of an organ or a body cavity, for example, the windpipe (trachea) of an intubated and ventilated patient, in particular via a sealing balloon element, wherein in the exemplary case of the dynamic sealing of the trachea, a balloon-type foil body preferably formed with residual material in the diameter, i.e., exceeding the tracheal diameter, is in contact with the inner wall of the trachea in a sealing manner and with a pressure that is as constant as possible; in doing so, fluctuations in the balloon volume, which are caused by fluctuations in the intrathoracic pressure relating to the mechanics of breathing, are compensated as quickly as possible by supplying volume from an extracorporeal reservoir or an extracorporeal source so that the tracheal secretion sealing of the balloon is thereby kept continuous.

BACKGROUND OF THE INVENTION

A fundamental with problem with the organ-compatible, efficiently sealing closure or with the space-filling tamponade of organs or cavities with a balloon-type element that is filled extracorporeally is an ongoing, more or less strongly pronounced motility of the organ itself. Organs or body cavities that are restricted in terms of muscular connective tissue frequently exhibit a characteristic movement dynamic, or are typically subject to the dynamics of adjacent organs or structures. For a continuously acting closure of the organ lumen, these types of inherently motile or correspondingly motile organs require a special regulating mechanism which reacts rapidly to fluctuations in the organ diameter and/or to changes in the tone of the organ wall and compensates for said fluctuations/changes. The mechanism must act as synchronously as possible to the respective change in diameter or tone in the organ and maintain, via an optimally rapid supply or even removal of filling medium in the balloon, the closing or sealing properties thereof.

The problem of a dynamically adapting sealing of a hollow organ can be illustrated using the example of the human windpipe. The windpipe (trachea) is a tubular structure formed of cartilaginous, connective-tissue and muscular-connective-tissue portions. It extends from the lower end of the larynx to the bifurcation into both main bronchial tubes. The forward and the lateral portions of the windpipe are stabilized in the process by clasp-like, approximately hoof-shaped structures, which are in turn connected to one another in the longitudinal direction by connective tissue layers. On the rear-wall side, the windpipe lumen is completed by the so-called Pars membranacea, which is made of continuously muscular-connective-tissue layers without reinforcing elements integrated therein. Lying closely against it dorsally is in turn the muscular-connective-tissue food pipe (esophagus).

The upper third of the trachea is normally situated outside the rib cage (thorax), while the two lower thirds are inside the thoracic cavity demarcated by the rib cage and the diaphragm. The lower thoracic portion of the trachea is thus subject in a special manner to the pressure fluctuations in the chest cavity, which arise in the course of "thoracic breathing work" of a patient who is breathing spontaneously without support or even of a patient breathing with mechanical assistance.

With the inhalation (inspiration) of the patient, the thoracic volume is increased by the lifting of the ribs and the simultaneous lowering of the diaphragm, whereby the intrathoracic pressure prevailing in the thorax drops. The pressure drop in the thorax leads to the influx of respiratory air into the elastically expanding lung following the thorax.

The drop in the intrathoracic pressure that accompanies the thoracic volume increase causes pressure fluctuations corresponding to the thoracic respiration of the patient, in sealing and/or tamponading balloon elements, which are positioned in the thoracic cavity, and are pressurized there with a specific filling pressure. This is observed for example in the case of the sealing balloon elements (cuffs) of tracheal tubes and tracheostomy cannulas, which seal the deep air passages against inflowing secretions of the throat, and make a positive pressure ventilation (PPV) of the patient's lung possible.

The cyclical intrathoracic pressure fluctuations produced by the patient during thoracic respiration can move the sealing-effective pressure in the balloons of ventilation catheters into regions in which a sufficient sealing against the secretions of the throat and the gastrointestinal tract is no longer guaranteed. The cuff pressure in the course of thoracic independent respiration of the patient can under some circumstances also assume sub-atmospheric values, which almost correspond to the respectively acting thoracic pressure. In this regard, see C H Badenhorst, "Changes in tracheal cuff pressure in respiratory support," CritCareMed, 1987; 15/4: 300-302.

While the sealing performance of conventional tracheal tube cuffs made of PVC correlates closely with the filling pressure currently prevailing in the cuff and, already in a pressure range of 30 mbar descending to 15 mbar, results in a drop in the sealing performance correlating hereto, tracheal tube cuffs made of polyurethane that are manufactured to be especially thin-walled have a substantially more stable sealing efficiency if the filling pressure prevailing in the cuff drops from 30 to 15 mbar; see G L Bassi, CritCareMed, 2013; 41: 518-526.

However, the filling pressure range of 15 to 5 mbar, which can be achieved virtually from breath to breath already in the case of moderately forced breathing work, is of essentially greater significance for the secretion sealing efficiency of tracheal cuffs. Even though sealing-optimized, micro-thin-walled PUR cuffs also offer good sealing performance at approx. 10 mbar of filling pressure, however, with pressure drops to under 10 mbar or to sub-atmospheric intrathoracic pressure values, they do not protect against inflowing subglottic secretion.

A closure technology of the windpipe using a cuff-type sealing balloon that can be manufactured cost-effectively, acts atraumatically and in an efficiently sealing manner over sufficiently broad filling pressure ranges, synchronously following the independent respiration of the patient is not available yet. Even though the prior art describes the most diverse designs of extracorporeal, filling-pressure-regulating devices for tracheal ventilation catheters, an actually synchronous (i.e., effectively from breath to breath) adaptation of the sealing pressure to alternating thoracic pressures, such as those that prevail during the independent respiration of the patient, does not currently exist in the prior art, however.

In the case of conventional ventilation catheters, the filling of the tracheal sealing cuff normally takes place using small-lumen, channel-like supply lines extruded into the wall of the catheter shaft. The small cross sections of the filling lines of approx. 0.5 mm normally do not ensure a volume flow of the filling medium pressurizing the cuff that is large enough to maintain the tracheal sealing of the cuff over a complete respiration cycle of the patient. Even technically intricate, electronically controlled regulating mechanisms, like for example the CDR 2000 device made by Logomed GmbH (no longer commercially available), likewise offer only an inadequate sealing efficiency due to the traditional small lumen of the supply line between the sealing balloon element and the regulator placed outside the body.

U.S. Pat. No. 5,235,973 describes a relatively intricate, electronically controlled regulation technology, which is geared towards an especially rapid pressure regulation in a sealing catheter balloon element. It describes, among other things, preferred cross sections of the supply line, which connects the catheter balloon to the pressure-regulating device. The cited diameters are in a range of approx. 2 to 3 mm. To reduce the flow resistance inside the supply line to the tracheal sealing cuff, which is essentially determined by the diameter of the extruded, supplying lumen that is integrated into the catheter shaft, PCT/IB2015/002309 and PCT/IB2016/001643 propose correspondingly dimensioned supply line cross sections.

However, it has turned out that supply line cross sections alone do not constitute a guarantee for a pressure equalization that is as rapid as possible in an intracorporeal sealing balloon, but that the entire structural embodiment of the flow channel between an intracorporeal sealing balloon, on the one hand, and of an extracorporeal regulating device, on the other, has an impact on the achievable flow rate and thus on the short-term displaceable filling pressure volume. Neither U.S. Pat. No. 5,235,973 nor PCT/IB2015/002309 nor PCT/IB2016/001643 address this problem.

These disadvantages of the described prior art resulted in the problem that instigated the invention of developing the flow channel between an intracorporeal sealing balloon, on the one hand, and an extracorporeal regulating device, on the other hand, in such a way that a pressure equalization that is as rapid as possible can be achieved in an intracorporeal sealing balloon.

SUMMARY OF THE INVENTION

The solution to this problem succeeds as a part of a device for the volume-compensating sealing of a hollow organ or an anatomical space that is in sync with organs, comprising (i) an intracorporeal balloon-type foil body formed to a residual dimension, i.e., exceeding the anatomical dimension of the organ or the respective space, and having sealing surfaces, which contact the wall of the respective hollow organ or space when the unexpanded balloon-type foil body is free of tension at least in regions while forming folds, while the foil-type balloon body is itself filled with a filling medium under a maximum target pressure of 50 mbar, preferably under a maximum target pressure of 40 mbar, in particular under a maximum target pressure of 30 mbar, (ii) a tube or other shaft, which rests on the balloon-type molded body, (iii) an extracorporeal regulating device with a volume reservoir and/or a pressure source for the filling medium, as well as (iv) a flow connection between the intracorporeal balloon-type foil body and the extracorporeal regulating device, which runs at least in regions in or along the tube or other shaft, in that the flow connection between the intracorporeal balloon-type foil body and the extracorporeal regulating device in the region of its progression in or along the tube or other shaft including a transition region from the tube or other shaft to a progression that is detached therefrom, is free of right-angled deflections, so that a laminar flow can form there and within a latency period of 200 ms or less, for example of 100 ms or less, preferably of 50 ms or less, in particular of 25 ms or less, the additional filling quantity of the filling medium needed in the balloon-type foil body can be supplemented, in order to compensate for fluctuations of the balloon filling pressure and/or of the balloon volume and/or of the pressures and forces bearing on the balloon-type foil body, so that the sealing or the space-filling tamponade of the hollow organ or of the space is maintained under dynamically alternating fluctuations of the balloon filling pressure with a pressure drop in the balloon-type foil body of 30 mbar.

The invention therefore takes into consideration the special requirement of preventing flow-reducing transitions and obstacles inside the supply line leading to the balloon or those that impede the optimally rapid pressure equalization between the sealing balloon and the regulator.

The inventor recognized that in particular the specific structural design of the transition of the shaft-integrated supply line in a hose-shaped supply line attached to the shaft, or even the specific structural design in the region of the exit of filling medium from the shaft-integrated supply line into the cuff, can reduce the volume flow and delay it in a sealing-relevant way. Above all, in the case of pressure equalization from an extracorporeal reservoir that is pressurized isobarically to the sealing cuff, flow-inhibiting transitions are problematic because of the normally small pressure differences driving the volume flow. The resulting delay in the case of pressure equalization between two compartments communicating with each other (the reservoir and cuff) precludes a continuously reliable seal. The cyclically adjusting pressure gradients move in a range of a few millibar, typically in a pressure range of approx. 5 to 30 mbar. The pressure gradient driving the volume flow from the reservoir or from the volume source to the cuff therefore requires the specially flow-optimized design described in the following of all components and all transitions between the components, from which the supply line between the reservoir and the cuff is composed in its entirety.

It has proven to be favorable if the tube or the other shaft consists of a material that is flexible in a such a restricted manner that it can bend but cannot kink. Therefore, the tube or the other shaft is able to adapt to the anatomy of a patient in an optimal manner, on the one hand, without its functioning being capable of being impaired. In particular, a kink could substantially delay a shifting of volume or even make it impossible.

Since for example steps, ridges, uneven surfaces or other unsmoothed structures interrupt the laminar flow of the filling medium in a turbulent manner, the invention provides that the flow connection in the region of the tube or of the other shaft and/or in the region of a transition between different components is free of kinks and/or free of edges and/or free of steps and/or free of gaps and/or free of ridges and/or free of other abrupt elevations or depressions, so as not to impair the laminar flow.

The invention experiences an advantageous further development in that the flow connection in the region of the tube or of the other shaft is free of bends, whose bending radius in the longitudinal direction of the flow is less than 0.5 cm, for example less than 1 cm, preferably less than 2 cm, in particular less than 5 cm. Like kinks, narrow changes in direction of the flow channel can also have a negative impact on the achievable flow rate, in particular since the tendency to form vortices would thereby be increased, and for this reason, narrow bends of this sort should be dispensed with.

It is within the scope of invention that the cross-sectional area of the flow connection the does not decrease starting from the region of the tube or of the other shaft up till the extracorporeal regulating device. Any back-up within the flow channel reduces the achievable flow rate and should therefore be prevented.

Particular advantages are yielded in that the cross-sectional area of the flow connection increases in the transition region from the tube or other shaft to a progression that is detached therefrom. In such a case, a possibly higher pressure within the regulating device can spread in a virtually unrestricted manner up to the transition region into the tube, so that a maximum pressure difference is available there, in order to drive a maximum shifting of volume within the flow cross section that is restricted there.

It has been proven that the cross section of the flow connection in or along the tube or other shaft comprises an arch-shaped form, which preferably tangentially nestles a functional lumen inside the tube or other shaft, or coaxially surrounds it. On the one hand, thanks to such an embodiment, it is possible to retain a relatively circular overall cross section of the tube corresponding to lumina of the human body whose cross sections are for the most part also approximately circular; on the other hand, the advantage of an arch-shaped elongated cross-sectional shape of the flow connection is that penetrated liquid cannot occlude the flow channel over its entire cross-sectional area, which would be accompanied by a substantial impairment of the pressure equalization.

Only in the case of as high-volume as possible and generally speaking short, supplying components can an optimally delay-free, ideally laminar, flow of the sealing medium be established in conjunction with turbulence-minimizing transitions between the components, from a volume reservoir or from an electronically/electro-mechanically regulated volume source to the sealing balloon, and thereby maintain a sufficiently rapid, dynamic sealing of the trachea from breath to breath.

The invention allows an implementation in such a way that the flow connection in the region of the tube or other shaft is configured as one on whose outer side a line or hose line can be attached, so that the number of transitions between different components of the flow channel, where vortices could be triggered, can be reduced.

To accommodate an attachable line or hose line of this type, a trough-shaped groove or depression can be formed in the outer side of the tube or of the other shaft. The advantage of this would be that the flow channel that is important for the sealing of the balloon is not exposed in the region of the tube and thus could get squashed, but is arranged in a protected manner in a depression of the tube.

As a part of a preferred further development of the invention, the trough-shaped groove or depression comprises lateral undercuts, so that a line or hose line, which can be pressed in or inserted there, is fixed and cannot detach spontaneously, which thereby facilitates the handling.

In addition, there is the possibility that the line or hose line that can be attached to the outer side of the tube or of the other shaft is preformed in such a way that it fills the trough-shaped groove or depression and thereby supplements the adjacent outer contours of the tube or the other shaft in a manner than maintains the contour. In such a case, the relevant tube or shaft can also be placed atraumatically in a lumen of the human body in the region of the hose line.

The invention allows a further development to the extent that a component with a ramp-shaped or arch-shaped progression is provided, in particular inserted, in the transition region of the flow connection from a flow channel section formed in or integrated into the tube or in another shaft to a progression of the flow channel that is detached therefrom. The object of such a component consists of redirecting the flow of the filling medium, for example air, in said transition region gently and turbulence-free so as not to impair the laminar flow.

Pursuing this inventive idea, it can be provided that a detachable component is inserted, by means of a rearward, preferably mandrel-like prolongation arranged on a side facing away from the ramp, into a depression aligning with the flow channel section formed in or integrated into the tube or in another shaft. As a result, it can be ensured that this type of component is always aligned optimally and that gaps or edges that could impair the flow do not develop for instance due to a slanted position or the like. Naturally, this type of component can also be fixed in terms of position additionally by means of adhesive.

Moreover, it can be provided that a component with a tubular form and a gently bent progression made of a kink-resistant material is inserted in the transition region of the flow connection from a flow channel section formed in or integrated into the tube or in another shaft to a progression of the flow channel that is detached therefrom. It is also the primary responsibility of this type of component to provide for a gentle change in the flow direction in the transition region and to counteract the generation of a turbulent flow there.

If the outer cross section of the component with a tubular form is larger than the inner cross section of the flow channel section formed in or integrated into the tube or in another shaft, it is thus able to be frictionally fixed there under local widening of the flow channel section and thereby experiences a guiding alignment in the longitudinal direction of the flow channel formed in the tube or other shaft.

A preferred embodiment of the invention is characterized in that a component made of a thin-walled material that nestles the outlet of the flow channel in the tube or other shaft is inserted in the transition region of the flow connection from a flow channel section formed in or integrated into the tube or in another shaft to a progression of the flow channel that is detached therefrom. One object of such a component consists of serving as reinforcement in the region of the notch in the tube or other shaft whereby it is structurally weakened in regions, in order to prevent an undesired kink from developing there.

The invention experiences a special embodiment in that a hood-shaped component with lateral, saddle-like planar extensions is attached or inserted in the transition region of the flow connection from a flow channel section formed in or integrated into the tube or in another shaft to a progression of the flow channel that is detached therefrom, wherein the extensions can preferably be connected in a stabilizing manner, for example adhesively, to the tube shaft covered therewith. Said lateral, saddle-like extensions are also used for alignment with respect to the tube sheath or shaft sheath as well as for fixing on just said tube sheath or shaft sheath.

As a part of an especially preferred embodiment of the invention a component with a ramp-shaped or arch-shaped progression is covered by a hood-shaped component. According to the invention, several components of this type can be combined with each other, in particular respectively a transition component inserted into the tube-internal flow channel or the lengthening thereof and a transition component fitting closely on the outer side of the tube or other shaft.

Comparable to the previously described transition elements, developed geometries can also be provided at the transition region between the distal end of the tube-integrated or shaft-integrated flow channel and the sealing balloon applied there to the tube or the shaft.

In general, a component arranged in the transition region of the flow connection from a flow channel section formed in or integrated into the tube or in another shaft to a progression of the flow channel that is detached therefrom, is provided in the region of the proximal end of said component with a socket for attaching or inserting a hose. If the hose has a radial enlargement there on its inner side, graduations can be prevented in this region.

In the segments or components of the supply line that are outside of the body, and whose structural design or dimensioning is not limited by anatomical parameters, the design of the supply line can generally be adapted to requirements relating to flow maximization. In particular, larger supply line cross sections can be realized. In the case of the described example of a tracheal tube or a tracheostomy cannula, there are anatomically induced limitations in the supply lines to the tracheal sealing cuff primarily in the region of the hose-like or tubular shaft components bearing the cuff. In particular, the level of the vocal folds (glottis) is limiting for the dimensioning of the tube shaft. It is the narrowest location in the air passages and predetermines the possible dimensions of the respectively possible outer tube diameters, and therefore also the diameters of the inner tube lumina extruded into the shaft. The cross-sectional area of the tube lumen used for ventilating the lungs must always be maximized because of the breathing resistance during ventilation that must be kept as small as possible. At the intubated vocal fold level, a certain residual space to the tube shaft normally remains in the dorsal region, wherein the vocal folds open triangularly spread out in the manner of a curtain from the ventral to the dorsal in a tent-like manner, and, on the base of the tent-like curtain or the glottis, free up a gusset-shaped region between the outer wall of the tube shaft and the base of the glottis. Said region can be used for additional and/or enlarged shaft-integrated lumina in line with a flow-optimized supply or even removal of a filling medium to the cuff. To this end, the invention proposes, among other things, an approximately barbell-shaped profile of a supply line in the dorsally positioned rear wall of the tube shaft, whose special, lateral enlargements of the barbell-shaped cross section fill out or use this residual space.

In the ideal structural form of the respective tube or the respective cannula, the length of the shaft-integrated supply line to the sealing balloon element is designed to be as short as possible, and extends from the opening of the supply line in the cuff to a point at a distance directly above, for example 2 to 3 cm, from the glottis. A hose lumen or other line lumen that is considerably enlarged in relation to the shaft-integrated lumen and has a correspondingly reduced flow resistance can already be attached in the supra-glottis hypopharynx.

A filter and/or a vapor barrier can preferably be provided extracorporeally in the flow connection. For example, the extracorporeal regulating device can be protected from penetrating moisture by means of the vapor barrier.

If a connector with an inner lumen is provided extracorporeally in the flow connection, the inner lumen thereof should preferably comprise a constant cross-sectional area over the entire length of the connector in a connected state of the subcomponents thereof.

It has been proved that the minimum clear inside cross-sectional area in the extracorporeal flow connection is larger than the minimum clear inside cross-sectional area of the intracorporeal flow channel section formed in or integrated into the tube or in another shaft, for example at least 1.1 times as large as the minimum clear inside cross-sectional area of the intracorporeal flow channel section, preferably at least 1.2 times as large as the minimum clear inside cross-sectional area of the intracorporeal flow channel section, in particular at least 1.3 times as large as the minimum clear inside cross-sectional area of the intracorporeal flow channel section. Such a cross-sectional enlargement makes it possible to further optimize the flow rate.

The invention strives for continuous pressure stabilization in the tracheal cuff at a target value, which can be set in a variable manner by the user or specified in a fixed manner by the specific design of the device, in a range of 20 to 40 mbar, preferably of 30 mbar, a maximum time delay of approximately 10 to 20 milliseconds, beginning from the point in time of the initial excursion of the thoracic pressure during the patient's active inspiration from a mechanically-ventilated rest position to a pressure level below said rest position. After a maximum of 20 milliseconds (ms), the respective excursions of the balloon sealing pressure occurring from breath to breath should return to the target value.

A constructively simply arrangement is obtained in that the pressure in a volume reservoir of the extracorporeal regulating device is set to the target pressure value for the balloon-type foil body. In such a case, even without an active regulation, it is ensured that the pressure in the sealing balloon cannot increase to values that are too great.

In such a case, an element with a valve function and/or a flow-directing function can be provided in the flow connection, which element is preferably oriented in such a way that it opens in the case of a negative pressure in the balloon-type foil body as compared to the pressure in a volume reservoir of the extracorporeal regulating device and allows a rapid volume flow into the balloon-type foil body, in particular even without an active regulation.

So that an excess pressure in the balloon-type foil body as compared to the pressure in a volume reservoir of the extracorporeal regulating device can gradually dissipate, a throttling element should be connected in parallel to the element with a valve function and/or a flow-directing function.

In the combination according to the invention of a sealing balloon, the shifts of volume to the sealing balloon component required for pressure stabilization are driven with a flow-optimized supply line to the sealing balloon that is integrated into the shaft hose of the catheter bearing the balloon, via a volume reservoir pressurized extracorporeally at a constant pressure, or via a mechanism acting permanently in a pump-like and/or reservoir-like manner to provide a volume with a constant pressure in another manner.

The respective sealing pressure in the pressurized combination of the balloon and the supply line can for example be generated and maintained by a gravity-based or spring-force-based mechanism, which acts on a balloon-like or bellows-like reservoir component in a manner that compresses or pressurizes the filling medium contained therein through the effect of force on the outer shell of the reservoir component. The balloon, supply line and reservoir are connected in this case to form a closed system. The filling and emptying of the system takes place via a filling valve that is preferably integrated into the reservoir.

The pressurizing of a reservoir component can also take place using a valve mechanism that is permanently connected to the reservoir, and driven in a pump-like manner or electromechanically, for example piezo-electrically.

As an alternative, the filling pressure prevailing in the system can also be produced by a reservoir balloon expanding elastically in a specific manner.

During filling with a specific initial volume, the shell of the balloon-like component transitions to an expansion status, which receives the volume contained in the balloon under a pressure that is specifically determined structurally, and which corresponds to the desired target sealing pressure in the system. With an increase in the filling volume of the balloon, it expands further in a characteristic "isobaric" manner, wherein the filling pressure adjusting in the reservoir balloon does not increase beyond a specific volume range or the respective target pressure is maintained. The reservoir balloon therefore keeps volume in "reserve," wherein the pressure of the filling medium in the "isobaric reserve range" remains constant. With these types of volume-expandable reservoir balloons manufactured for example of polyisoprene, it is possible to dispense with a force acting externally on the reservoir shell. A corresponding technology is described for example in PCT/EP2013/056169.

Moreover, electronically or electromechanically regulated components that are connected to the balloon and the supply line to the balloon to form a communicating closed system are conceivable, which components convey the volume, that is required as part of the regulation of the balloon sealing, under constant pressure (isobarically) to the system or make it available to the system without the interconnection of a quasi "buffering" reservoir-type component, in the manner of a "source."

In addition to such constant-pressure sources, which generate a pressure that corresponds to the required sealing pressure in the tracheal cuff, regulating systems that are reservoir-like or source-like can also be attached to the combination of the balloon and the supply line to the balloon, which operate with pressure gradients, or which exceed the pressure range of 20 to 40 mbar. Such systems keep for example a pressure of 100 mbar available and displace the filling medium in a corresponding accelerated manner driven by gradients that are high relative to the target pressure. The accelerated volume flow directed to the cuff can be set for example by an electronically controlled proportional valve. In this case, precise, piezo-electrically driven valves in particular provide a foundation. The valves are small, noiseless and have a low power consumption. In addition, piezo-electrically driven pumps, which also noiselessly build up a reservoir pressure of to 100 mbar, can be connected upstream from the valves.

The pressure of a pressure source for the filling medium in the extracorporeal regulating device, in particular upstream of a regulating valve, can be set to a pressure value above the target value for the balloon-type foil body, for example to a pressure value of 100 mbar or more, preferably to a pressure value of 200 mbar or more, preferentially to a pressure value of 500 mbar or more, in particular to a pressure value of 1 bar or more, or even to a pressure value of 2 bar or more. The pressure differential to the considerably lower pressure in the sealing balloon then drops for the most part via a regulating valve, which, depending on the embodiment, either opens only slightly as needed or is operated with a timing in such way that the pressure downstream of the valve is regulated.

A pressure sensor can be arranged in the balloon-type foil body to detect the actual pressure value.

A pressure sensor of this type in the balloon-type foil body should be connected or can be connected via cable to the extracorporeal regulating device, preferably wherein the connecting cable is laid inside the tube or other shaft in a possibly additional lumen or inside the flow connection. In addition, a radio connection would of course also be conceivable, for example via Bluetooth, which, however, is significantly more costly and more likely to be prone to failure than a cable connection.

The invention furthermore provides that the extracorporeal regulating device comprises an active regulator, preferably an electronic regulator, in particular a two-point regulator, which in particular is designed in such a way that, in order to adjust the pressure inside the balloon-shaped foil body that was detected as an actual value as constantly as possible to a predetermined or predeterminable target value.

Specially optimized closed control circuits can be produced in conjunction with active, electronically controlled regulators, wherein the pressure-recording sensors are integrated inside the sealing balloon component and preferably connected to the controller of the regulator unit via a cable connection. These types of back-coupled systems can also be designed for the active removal of volume from a balloon, wherein a negative pressure gradient is generated by the regulator, parallel to an excess pressure gradient, so that, as the case may be, volume can flow off from the sealing balloon directed toward the regulator in an accelerated manner.

An electronic two-point regulator used in the course of the invention can be operated with a fixed timing frequency of for example between 100 Hz and 1000 Hz, wherein respectively a valve, for example a piezo valve, is alternatingly opened and closed between a pressure source for the filling medium with an appropriate frequency, wherein preferably the pulsation ratio between the opening phase and the closing phase can be influenced by the regulator, in particular as a reaction to the difference between a predetermined or predeterminable target pressure value, on the one hand, and the actual pressure value measured inside the balloon-type molded body, on the other hand. Because of the regulator valve that is used in the process, it is possible for there to be quite a significant pressure difference between a possible high pressure upstream of such a valve, and the lower pressure downstream of the valve that is regulated by the pulsation.

The hollow organ or the anatomical space is preferably the trachea or the esophagus of a patient. The described principle of the flow-optimized, latency-minimizing volume compensation or volume stabilization in a sealing balloon that is placed in a trachea, however, can also be used in an analogous manner in the case of the sealing tamponade of the esophagus of a spontaneously breathing patient. The pressure fluctuations that also correspond to the independent respiration of the patient in a balloon placed in the esophagus and acts in a tamponading sealing manner are generally even more pronounced than is the case with a balloon that is placed in the trachea. They correspond in a good approximation to the respectively prevailing intrathoracic pressure. To establish the most efficient possible sealing balloon tamponade in the esophagus, the invention proposes, as a structural variant, a segmentation of the sealing balloon. Whereas the distal segment of the balloon sealing the esophagus extends over the section of the esophagus between the upper and lower sphincter, a tapered balloon segment connects toward the proximal, which optionally extends to the proximal end of the catheter bearing the balloon. The resulting gap space between the shaft and proximal balloon segment can be dimensioned generously. It permits the filling of the distal balloon segment virtually around the catheter shaft and makes correspondingly flow-optimized, rapid shifts of volume possible, even in the case of low differential pressures driving the volume flow extracorporeally to intracorporeally. These types of dynamically pressure-regulated balloon tamponades can be used in particular on trans-esophageally placed probes for gastric feeding and/or decompression of the stomach. The connection to an isobarically acting volume reservoir or to a volume source regulated by a differential pressure can be accomplished in a design that is analogous to sealing the trachea.

In addition, the invention provides that the sealing balloon element consists of a thin-walled balloon foil made of polyurethane, which in the segment directed towards the respective surface to be sealed has a wall thickness of 5 to 30 μm, preferably of 10 to 20 μm. Furthermore, the sealing balloon element can consist of PUR with a material durometer according to Shore of 70 A to 95A, and/or with a material durometer according to Shore of 54 D to 60 D. On the one hand, this type of material can be slightly residually preformed, so that it does not need to be transformed into an elastically expanded state for sealing.

Finally, it corresponds to the teaching of the invention that the sealing balloon element comprise a multilayer wall structure, wherein at least one material layer has special barrier properties for water vapor and/or air, wherein the barrier layer consists for example of EVOH. As a result, the penetration of moisture that gets deposited in the supply line and could impede a rapid shifting of volume there can be prevented, for example.

BRIEF DESCRIPTION OF THE DRAWINGS

The following figures explain the inventive content based on concrete structural embodiments, which show.

DETAILED DESCRIPTION OF THE PREFERRED EMBODIMENTS

Figure 1:
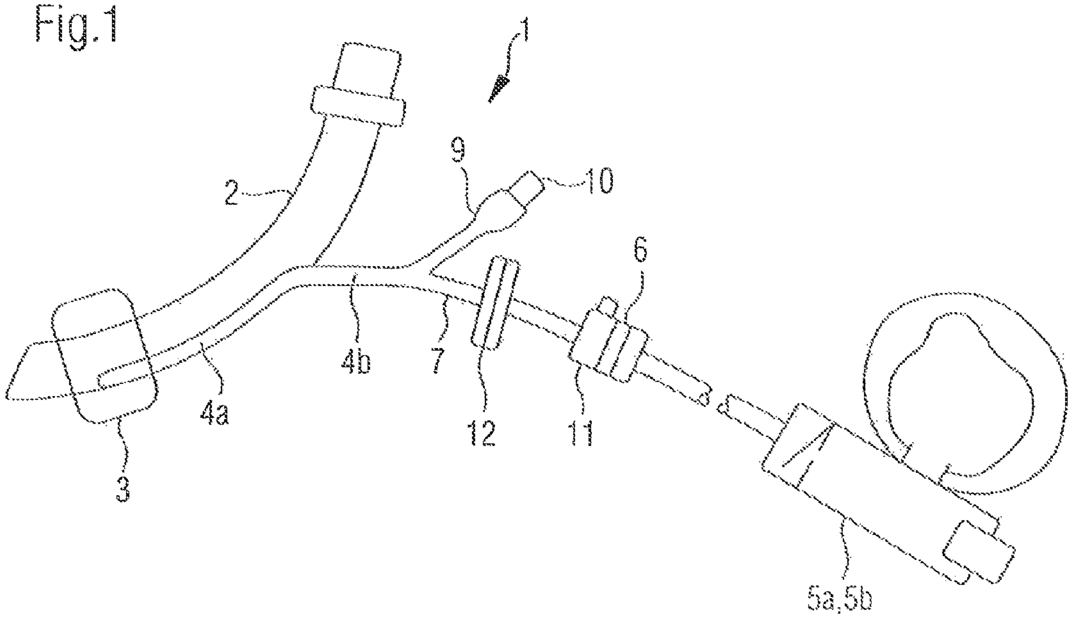
FIG. 1 An exemplary structural form of a tracheal tube according to the invention, which integrates a selection of flow-optimizing components and features, which facilitate a rapid shifting of filling medium to the sealing balloon even with a small pressure difference driving the volume flow from the extracorporeal to the intracorporeal, or facilitate a dynamically adapting sealing of the trachea synchronous to the breathing work of the patient.

FIG. 1 describes by way of example a catheter according to the invention on the basis of a tracheal tube 1, consisting of a shaft element 2, which bears a tracheal sealing cuff 3 on the distal end, wherein this is connected via a shaft-integrated channel-like supply line 4*a*, which merges outside of the shaft into a filling hose 4*b*, to an extracorporeal volume reservoir 5*a*, which keeps the cuff pressurized with filling pressure or keeps a gaseous filling medium available with a tracheal target sealing pressure, or connects to an electronically regulated volume source 5*b*, which adjusts the tracheal target sealing pressure via a pressure difference generated by the volume source, or the pressure generated by the volume source exceeds the tracheal target sealing pressure. The reservoir or the source is attached by a connector 6 to the filling hose 4*b*. In addition to a leg 7 that concludes with the connector 6, the filling hose 4*b* comprises a further leg, which merges into a pilot balloon 9, which is provided with a filling valve 10. Built into the leg 7 is a closing mechanism 11 that optionally can be operated manually by the user, which mechanism makes it possible to connect the reservoir unit or source unit to a tube pressurized with filling pressure that is already intubated in the patient without a pressure drop in the tracheal sealing cuff. To prevent the transfer of condensation water from the supplying system into the respectively pressure-regulating unit, a correspondingly gas-permeable element 12 which has water-repellant properties is optionally integrated into the leg 7. As an alternative or a supplement to the water-repellent function, the element 12 can also act as a microbial filter. The overall cross-sectional area of the shaft-integrated channel 4*b* corresponds to a circular cross section of at least 2 mm, preferably 3 to 4 mm. The cross-sectional area of the inner lumen of the filling hose 4*b*, as well as of the leg 7, and of the hose line connecting to the leg up to the reservoir corresponds to a circular diameter, which preferably exceeds 2.0 mm, preferably more than 3.0 mm and especially preferably comprises more than 3.5 mm.

Figure 2A:
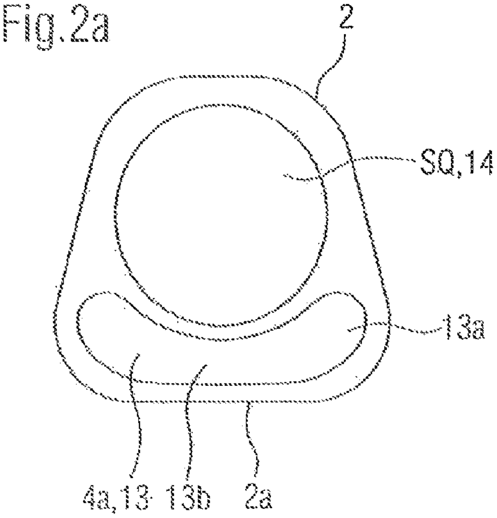
FIG. 2*a* A transversal section through the shaft of a tracheal tube, with a special design of the lumina integrated into the shaft, wherein the overall cross-sectional area of the supply line to the tracheal sealing cuff, which supply line is integrated into the wall of the tube, is designed to optimally large, and wherein transient, lumen-occluding relocations of the supply line from water condensation that penetrate into the supply line are prevented due to a special, barbell-shaped profile.

FIG. 2*a* shows a design of the shaft element 2, wherein the supply line 4*a* integrated into the shaft wall comprises a special barbell-shaped profile 13 in a transversal section, which maximizes the overall cross section of the supply line, which cross section determines the flow resistance in an optimal manner. The supply line is extruded into the dorsal portion 2*a* of the tube shaft i.e., in the case of the usual design of a tracheal tube according to Magill, lies in the so-called large curvature of the shaft, which rests on the broad base of the vocal fold trigonum. The overall profile of the shaft SQ produced by the barbell-shaped filling line comprises a corresponding broadening of the dorsal "base" of the tube profile. The wide base of the large curvature makes it possible for the ventilating lumen 14 of the tracheal tube, which is integrated ventrally in the shaft, to be able to be maintained in terms of its round or slightly oval shape as well as its cross-sectional area. The terminal enlargements 13*a* of the filling line lie respectively in the outer angles of the base of the shaft profile that is directed dorsally. In the case of a properly intubated tube position, the broadened rear wall thereof fits closely on the wide base of the glottis in an approximately congruently-shaped manner. The lateral enlargements of the profile are connected by a tapered, bridge-like, center segment 13*b*. The communication of the enlargements through the center bridge prevents condensation water that penetrates into the filling line from causing an occlusion of the lumen that supplies the cuff due to capillary forces, whereby the continuous connection of the regulating unit to the cuff can be impaired. A fluid level that forms in a barbell-shaped profile normally travels through the bridge-like connection of the one profile enlargement to the enlargement arranged in parallel, whereby a flow-effective occlusion of the filling line can be precluded to a large extent. In the preferred design, the enlargements 13*a* each have a diameter of 1.5 to 2.5 mm, preferably of 1.5 to 2.0 mm. The bridge 13*b* connecting the lumina has a height of approx. 0.5 to 1.0 mm.

Figure 2B:
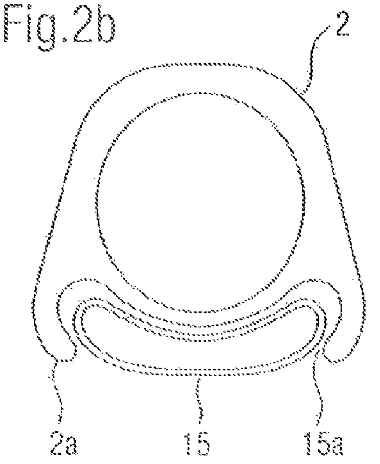
FIG. 2*b* A structural variation of the embodiment depicted in FIG. 2*a*, wherein the supply to the cuff takes place through a separately manufactured hose, which comprises the barbell-shaped cross section described in FIG. 2*a*, but is inserted into a congruently shaped recess of the dorsal tube shaft and fixed there.

FIG. 2*b* shows a structurally modified design of the profile 13 described in FIG. 2*a*, wherein, as a separately manufactured hose 15, the barbell-shaped supply line is inserted into a congruently-shaped recess 15*a* in the dorsal wall of the tube or in the large curvature thereof, and fixed there. The advantage of this design is that the hose can be guided out of the shaft of the tube above the level of the vocal folds and can be guided further as the filling hose without a structural interruption. The hose element 15 thus connects the cuff of the tube to the elements of the supply line that are integrated extracorporeally in a continuous, flow-optimized manner, wherein flow-inhibiting transitions are prevented. To maximize the inner diameter, the hose element 15 can consists of a thin-walled material that spontaneously elastically straightens, such as polyurethane for example, wherein preferably material hardnesses in a range of 90A to 95A or 55 D to 60 D are used. The tube shaft itself consists preferably of non-elastically plastically deforming PVC.

Figure 3A:
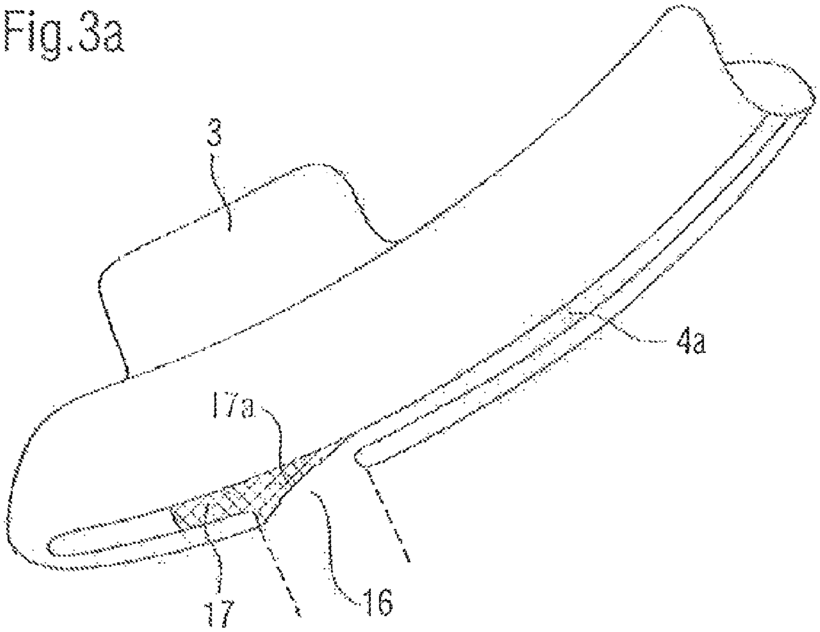
FIG. 3*a* A depiction of the distal section of a tracheal tube shaft according to the invention, which distal section bears the balloon, comprising a flow-optimized transition from a filling line integrated into the wall of the tracheal tube shaft to the inner space surrounding the balloon component via a ramp-like component.

FIG. 3*a* shows the transition from the shaft-integrated filling line 4*a* to the tracheal sealing cuff 3, wherein flow-inhibiting effects from turbulence when transferring the filling medium from the supplying lumen into the cuff are minimized, in that the deflection of the medium in an angle that is as flat as possible occurs or a transfer in a steep angle or right angle is avoided, such as is typically caused with the conventional design of tracheal tubes due to a simple tangential cut of the wall of the filling line.

The cut 16 of the filling line 4*a* is therefore lengthened in axial expansion thereof from 1 to 2 mm for conventional tubes to 4 to 10 mm, preferably 5 to 8 mm. Inserted into the distally extending opening of the cut of the supply line 4*a* is a component 17 closing the supply line, which forms a proximally descending ramp 17*a* in the opening, which guides the medium flowing to the cuff in a turbulence-free into the cuff. The ramp extends overs an axial length of 4 to 6 mm.

Figure 3B:
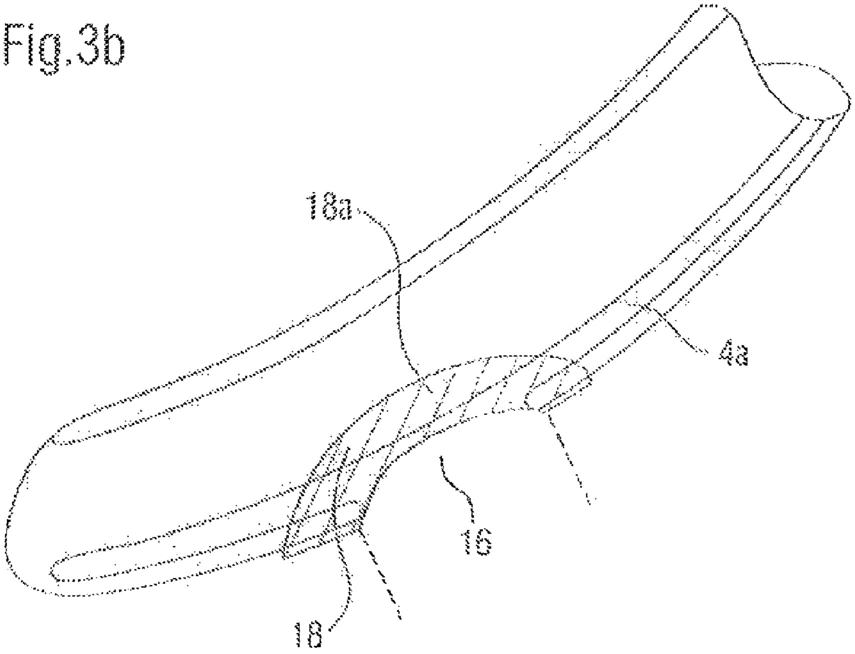
FIG. 3*b* A further embodiment of a flow-optimized transition from the shaft-integrated, channel-like supply line to sealing balloon, wherein the transition is designed in the form of a shell-like supporting component, which nestles on the outer perimeter of the tube shaft around the opening region of the shaft-integrated supply line and thus stabilizes the shaft wall in the opening region or prevents the shaft from kinking.

FIG. 3*b* shows a component 18, which as a supplement to the component 17 described in FIG. 3*a*, is integrated in the region of the lengthened cut in the region of the opening 16 of the supply line for axial stabilization of the tube shaft. The component 18 consists of an especially thin-walled material with a high hardness, and circularly nestles the outer contour of the section, in a saddle-like manner on the lateral surfaces 18*a* thereof. The component is preferably produced in an injection molding process. The previously described, lumen-closing and flow-guiding component 17 can be structurally connected to the component 18 or be integrated into said component.

Figure 4A:
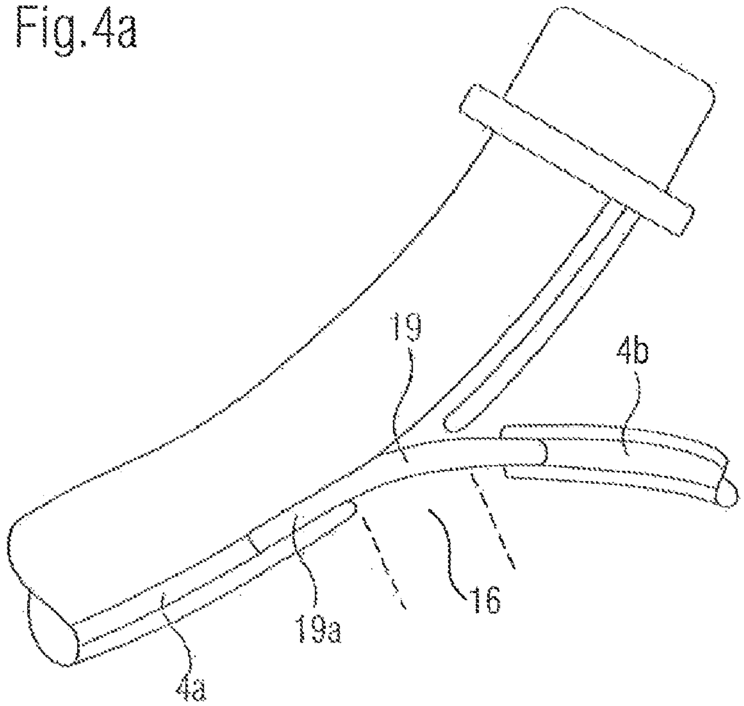
FIG. 4*a* An embodiment of the invention with a flow-optimized or current-optimized transition from a filling hose to the shaft-integrated, channel-like supply line lumen.

FIG. 4*a* shows a special transition element 19, which leads the shaft-integrated supply line 4*a* to the filling hose 4*b* or connects the lumen of the supply line to the lumen of the filling hose. The supply line 4*a* is cut tangentially in the transition region and open over a length of approximately 5 mm. The transition element 19 is preferably fabricated of a kink-resistant material that is designed to be thin-walled, and can be glued with solvent, and comprises a distally directed prolongation 19*a*, whose outer dimension is enlarged in relation to the dimension of the diameter of the filling line integrated into the shaft of the tube, and thus is inserted with a certain tension into the supply line 4*a* opened by the tangential cut. The inner lumen of the mandrel-like prolongation corresponds to that of the supply line, whereby the formation of step-like structures or a turbulent flow arising in the transition region can be prevented.

In the proximal region of the transition element 19, said element optionally comprises a sleeve-like receptacle for the filling hose 4*b*, wherein the hose is inserted into the receptacle in such a way and fixed by adhesion so that the inner lumen of the element 19 corresponds to the inner lumen of the filling hose 4*b*. The element 19 therefore ensures also in the region of the proximal connection that caliber transitions from the shaft-integrated supply line to the filling hose are prevented, and flow-reducing step formations are ruled out. In this especially flow-critical region, the element makes a laminar flow of the filling medium possible from the reservoir or the source to the tracheal sealing cuff. Furthermore, because of the element 19, transitions from circular cross sections of the filling hose 4*b* to flattened, oval, flat oval, or even barbell-shaped cross sections of the distal portion 19*a* of the transition element can be smoothed in a flow-optimizing manner.

The cross-sectional area of the filling hose 4*b* corresponds at least to the overall cross-sectional area of the shaft-integrated supply line 4*a*, but exceeds it in preferred embodiments.

Figure 4B:
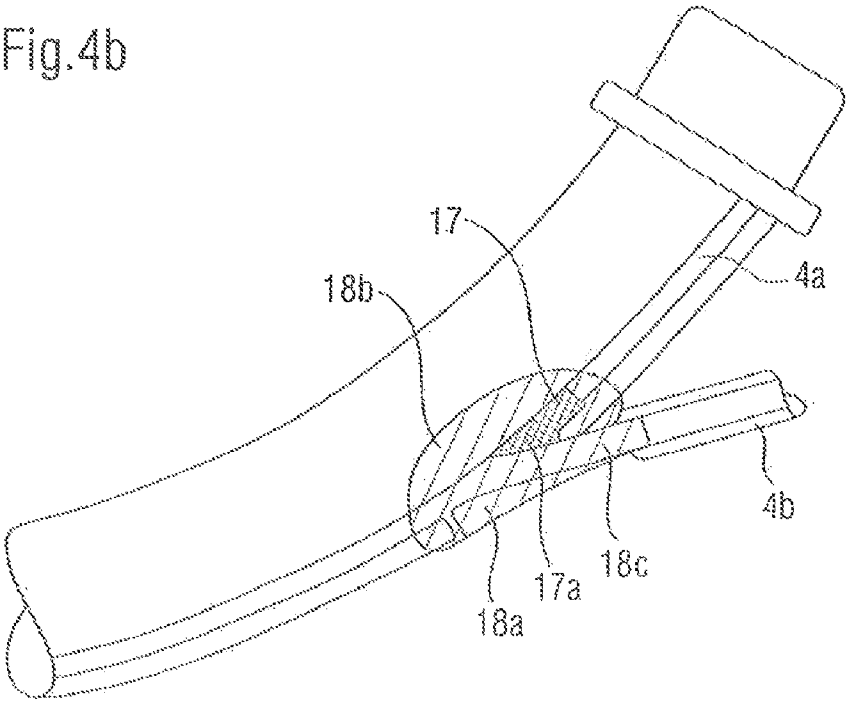
FIG. 4*b* Another embodiment of the transition from the filling hose to the shaft-integrated supply line lumen, comprising a hood-like component connecting the supply line and the filling hose to each other, which establishes a step-less, flow-optimized transition towards both connected lumina.

FIG. 4*b* shows a hood-like component 18*a*, which nestles the dorsal perimeter of the tracheal tube with a custom fit and covers the cut of the supply line 4*a* in a tightly sealing manner. The component comprises lateral, saddle-like, planar extensions 18*b*, which connect to the lateral wall of the tube shaft in a manner that stabilizes the tube shaft in the region of the cut. The hood-like component comprises a connecting piece 18*c* going off towards the proximal in a flat angle, which receives the filling hose 4*b*. The figure furthermore shows a component 17, which is inserted directed proximally into the supply line channel 4*a*, and closes it. Analogous to the ramp-like design in FIG. 3*a*, the connecting piece 18 forms a flow-optimizing ramp 17*a*, which extends from the proximal to the distal into the cut of the supply line, and is thereby correspondingly beveled.

Figure 5:
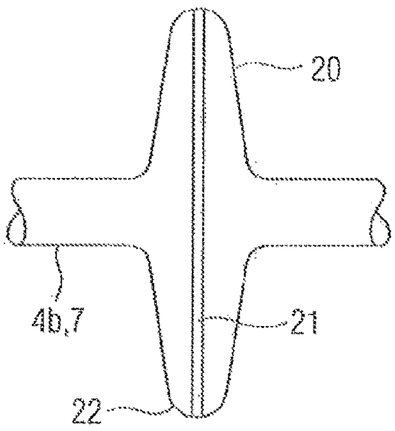
FIG. 5A longitudinal section of the vapor barrier and/or microbe barrier integrated into the filling hose.

FIG. 5 shows an optional vapor barrier 20 integrated into the filling hose 4*b* or the leg 7. The surface of the respective separating layer 21 is thereby selected to be so large that the flow resistance caused by the barrier function is compensated for and delays during pressure equalization in the cuff are prevented. The barrier layer comprises a diameter of at least 10 to a maximum of 25 mm, preferably 15 mm. The housing 22 is flat and designed to be discoid and thus reduces the residual space around the separating layer. The function of the vapor barrier ensures that water vapor and condensate are not able to penetrate into the region of the regulating unit and negatively impact the opening and closing behavior of the valves installed there. As an alternative or addition to the vapor barrier 20, a microbe-tight barrier layer can be installed in the housing 22.

Figure 6:
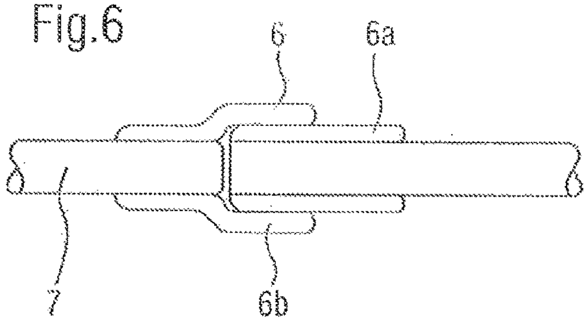
FIG. 6A structural form of a flow-optimized connector between the proximal end of the filling hose and the regulator.

FIG. 6 shows a special connector 6, which comprises a constant cross-sectional area over its entire inner lumen. By inserting the male part 6*a* into the female part 6*b*, a step-less, gap-less and ridge-free transition is thereby facilitated. The cross sections of the lumina connected to each other are identical in the region of the connection.

Figure 7:
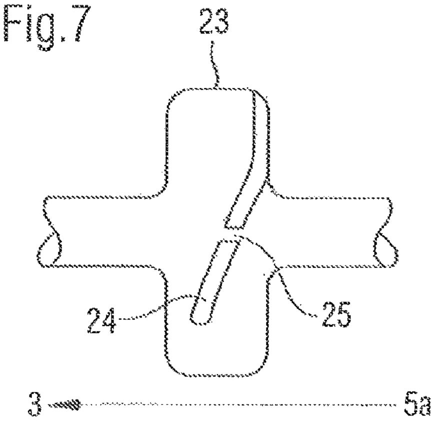
FIG. 7A longitudinal section through a smooth-running valve element with an optional retrograde volume equalization function.

FIG. 7 shows a unit 23 with a valve function, wherein the flow-directing function is preferably produced by a lobe-like, film-thin valve plate 24. In an open state of the valve, a cross-sectional area of the valve opening is adjusted which corresponds at least to the diameter of the line arranged distally to the valve, but preferably exceeds said line. The valve plate preferably has a hole-like perforation 25, which even in a closed state of the valve makes possible a reduced volume flow from the cuff to the regulating unit that opposes the main flow, so that transient excess pressure situations in the cuff can be balanced out by an appropriately delayed volume outflow from the cuff.

A backflow function acting in a correspondingly manner can occur alternatively with a channel-like connection arranged parallel to the valve plate, which makes a specific throttled outflow of medium from the cuff to the reservoir or to the source possible.

Figure 8:
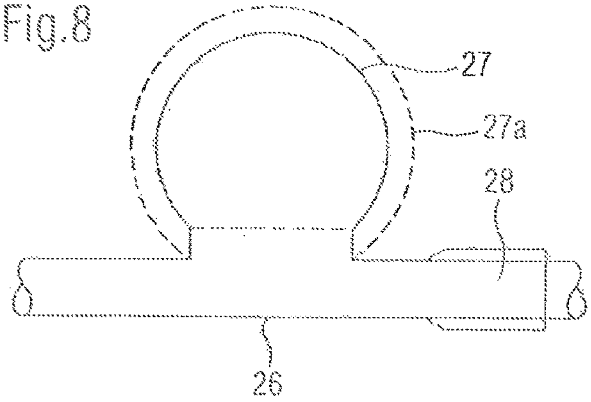
FIG. 8 An extracorporeal volume reservoir with isobaric volume expansion characteristics.

FIG. 8 shows a volume reservoir 26, which has a specifically volume-expandable reservoir balloon 27, which receives the filling medium with a constant isobaric pressure over a specific radial expansion region 27*a* of the balloon shell. The plateau pressure that adjusts during the expansion of the balloon shell is defined by the specific design or the material used and the geometry of the balloon. The respective plateau pressure in the reservoir corresponds to the target pressure prevailing in the balloon of for example 30 mbar. The pressure generated by the expanded reservoir balloon drives the volume flow to the sealing balloon element in the moment of a pressure drop in the balloon. The reservoir can be filled by a fill valve 28 preferably with air as the filling medium.

Figure 9:
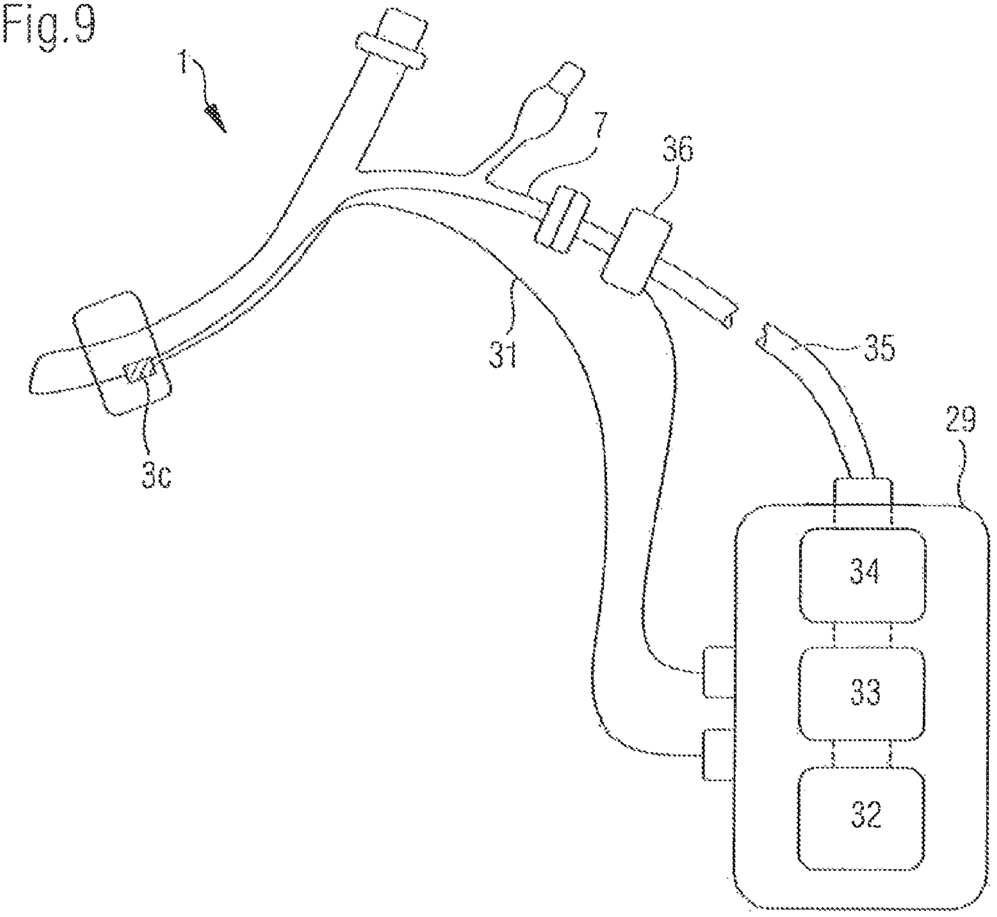
FIG. 9 An electronic/electromechanical regulating system coupled back in a direct manner with a tracheal sealing cuff, which accelerates the inflow of the filling medium, and optionally also the outflow thereof, over the hose line and channel line reaching from the regulator to the sealed cuff, via a flow-resistant compensating differential pressure, or wherein the pressure generated by the regulator exceeds the target pressure in the tracheal sealing cuff, and wherein the pressure in the cuff is recorded by an electronic sensor positioned inside the cuff and is fed to the regulator unit.

FIG. 9 shows a back-coupled regulating system 29, which is attached to a flow-optimized catheter 1 of the design type according to the invention. Inside the sealing balloon, the catheter has an electronic pressure sensor 3*c* permanently integrated there, which is connected via a cable connection 31 to the regulating system. The regulator itself consists of a pump module 32 with an optionally integrated reservoir 33 and at least one regulating valve module 34 with an integrated control unit. The user can enter target values and alarm values into the controller. As an option, the regulator can also have two pump systems, with a respectively attached reservoir, wherein the one reservoir keeps an excess pressure available and the other a negative pressure. The gradients or the differential pressure from the target value kept available in the regulator in the cuff are adjusted autonomously by the regulator in an optional design by a learning algorithm in such a way that the latency until reaching the target value in the cuff is in a range of 10 to 20 ms. Both the pump functions and the valve functions are preferably based on piezo-electric components, which can be operated precisely and rapidly, as well as quietly and in an energy-saving manner The supply line 35 to the leg 7 of the catheter preferably comprises an inner diameter which exceeds the diameter of the leg, and in an ideal case exceeds it by 30%, in order to thereby keep resistance-induced flow losses as small as possible. As an alternative to the cuff-integrated pressure sensor, a peripheral pressure-converting sensor 36 can be integrated into the supply line and be positioned in the immediate vicinity of the connector 6. With this design, it is possible to dispense with a sensor integrated in the cuff, wherein a certain delay in the regulating time must be accepted.

Figure 10:
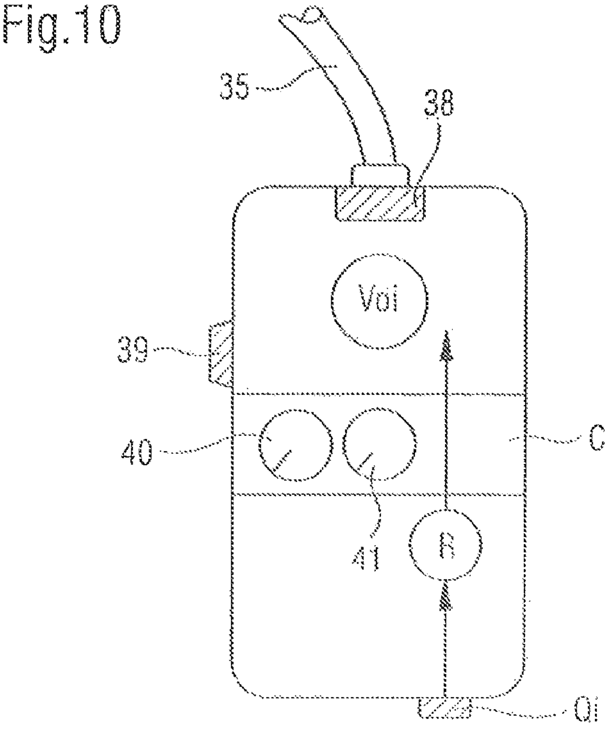
FIG. 10 An alternative, electronic/electromechanical regulating system, wherein the electronic sensor components recording the cuff pressure are integrated in the regulator unit.

FIG. 10 describes another regulator unit for continuously maintaining a sealing balloon filing pressure. The cuff of the tracheal tube is already formed during manufacturing to its required working dimension. The filling of the balloon takes place in the previously described flow-optimized or resistance-minimizing manner. The balloon is filled with gaseous medium. The hose supply line 35 from the regulator to the connector 6 should comprise a circular lumen with a diameter of at least 5 mm, in order to prevent flow-induced pressure losses and dampening effects between the balloon and regulator. The regulator unit consists of a single valve Voi that operates piezo-electrically, which both directs volume to the tamponading balloon as well as discharges volume therefrom. Connected upstream of the valve on the patient side is an electronically pressure-measuring component 38, which continuously detects the pressure in the balloon body and conveys it to the control unit C. The regulator unit does not have a measuring function of a pressure electronically measured directly in the balloon. Connected upstream of the valve on the side facing away from the patient is a pressure reservoir R integrated into the device or an external pressure source Qi, which keeps the filling medium available for example in a pressure range of 1 to 2 bar. The piezo valve Voi reduces this reserve pressure to approx. 10 to 30 mbar sealing pressure in the balloon. If the target pressure set by the user in the balloon is exceeded, it is detected by the component 38. The control unit C then opens the valve Voi, then discharges the filling medium, following the respective gradient, via an opening 39 to the environment. The unit has an adjustment option for the tracheal sealing target pressure 40 and a possibility for setting the respective volume flow 41 to or from the balloon.

List of Reference Numbers

| | |
|---|---|
| 1 | Tracheal tube |
| 2 | Shaft element |
| 2a | Rear-wall portion |
| 3 | Cuff |
| 4a | Channel-like supply line |
| 4b | Filling hose |
| 5a | Volume reservoir |
| 5b | Volume source |
| 6 | Connector |
| 6a | Male part |
| 6b | Female part |
| 7 | Leg |
| 8 | Leg |
| 9 | Pilot balloon |
| 10 | Filling valve |
| 11 | Closing mechanism |
| 12 | Gas-permeable element |
| 13 | Barbell-shaped profile |
| 13a | Terminal enlargement |
| 13b | Center segment |
| 14 | Ventilated lumen |
| 15 | Hose |
| 15a | Recess with a congruent shape |
| 16 | Cut |
| 16a | Distal opening |
| 17 | Component |
| 17a | Ramp |
| 18 | Component |
| 18a | Lateral surface |
| 18b | Planar extension |
| 19 | Transition element |
| 19a | Distal portion |
| 20 | Vapor barrier |
| 21 | Separating layer |
| 22 | Housing |
| 23 | Unit |
| 24 | Valve plate |
| 25 | Hole-like perforation |
| 26 | Volume reservoir |
| 27 | Reservoir balloon |
| 27a | Filing region |
| 28 | Fill valve |
| 29 | Regulating system |
| 30 | Pressure sensor |
| 31 | Cable connection |
| 32 | Pump module |
| 33 | Reservoir |
| 34 | Valve model |
| 35 | Supply line |
| 36 | Sensor |
| 37 | Regulator unit |

-continued

List of Reference Numbers

| | |
|---|---|
| 38 | Component |
| 39 | Opening |
| 40 | Target pressure |
| 41 | Volume flow |
| C | Control unit |
| Qi | External pressure source |
| R | Pressure reservoir |
| SQ | Shaft profile |
| Voi | Valve |

The invention claimed is:

1. A device comprising:

a tracheal tube shaft;

a supply line partially integrated into the tracheal tube shaft, wherein, to partially integrate the supply line into the tracheal tube shaft, a hood-shaped component having planar extensions is inserted into a transition region of the supply line from a flow channel section of the tracheal tube shaft, wherein the planar extensions are adhesively coupled to the tracheal tube shaft;

a tracheal tube cuff coupled to a distal end of the tracheal tube shaft via the supply line, wherein the tracheal tube cuff has a balloon foil body that is filled with a filling medium, and wherein dimensions of the tracheal tube cuff enable a sealing surface of the tracheal tube cuff to contact a tracheal wall of a patient when the tracheal tube cuff is free of tension, wherein the hood-shaped component with planar extensions is inserted in the transition region of the supply line, and wherein the planar extensions are adhesively coupled to the tracheal tube shaft;

a pressure sensor configured to:

detect a pressure level inside the tracheal tube cuff; and convert the pressure level into an electronic signal; and a regulating device coupled to the pressure sensor, wherein the regulating device is configured to:

determine, based on the electronic signal, the pressure level inside the tracheal tube cuff; and compare the pressure level inside the tracheal tube cuff to a target pressure level; and based on the comparison, adjust, via the supply line, an amount of the filling medium inside the tracheal tube cuff to adjust the pressure level inside the tracheal tube cuff via the supply line.

2. The device according to claim 1, wherein the tracheal tube shaft comprises a flexible material that bends without kinking.

3. The device according to claim 1, wherein the transition region of the supply line is free of kinks that impair laminar flow.

4. The device according to claim 1, wherein the flow channel section of the tracheal tube shaft is free of kinks that impair laminar flow.

5. The device according to claim 1, wherein a cross-sectional area of the flow channel section of the tracheal tube shaft is constant.

6. The device according to claim 1, wherein a cross-sectional area of the flow channel section of the tracheal tube shaft varies at different locations.

7. The device according to claim 1, wherein a cross section of the flow channel section of the tracheal tube shaft has an arch-shaped form.

8. The device according to claim 1, wherein an outer side of the tracheal tube shaft is coupled to a hose line.

9. The device according to claim 8, wherein a trough-shaped groove is formed in the outer side of the tracheal tube shaft to facilitate coupling to the hose line.

10. The device according to claim 9, wherein the trough-shaped groove comprises lateral undercuts to prevent the hose line from spontaneously detaching.

11. The device according to claim 9, wherein the hose line fills the trough-shaped groove.

12. The device according to claim 1, wherein a detachable component with a ramp-shaped progression is inserted in the transition region of the supply line.

13. The device according to claim 1, wherein a component made of a thin-walled material nestles an outlet of the flow channel section of the tracheal tube shaft.

14. The device according to claim 1, wherein a component with a ramp-shaped progression or arch-shaped progression is covered by the hood-shaped component.

15. The device according to claim 1, wherein a component in the transition region of the supply line from the flow channel section of the tracheal tube shaft has a socket for attaching or inserting a hose.

16. The device according to claim 1, wherein a filter and a vapor barrier are included in the supply line.

17. The device according to claim 1, wherein the supply line comprises a connector with an inner lumen, wherein the inner lumen comprises a constant cross-sectional area over a length of the connector.

18. The device according to claim 1, wherein a minimum clear inside cross-sectional area in an extracorporeal portion of the supply line is larger than a minimum clear inside cross-sectional area of an intracorporeal portion of the supply line.

19. The device according to claim 1, wherein a pressure in a volume reservoir of the regulating device is set to the target pressure level.

20. The device according to claim 1, wherein the supply line includes a valve function element that is configured to open if the pressure level inside the tracheal tube cuff is less than a pressure level inside a volume reservoir of the regulating device.

21. The device according to claim 1, wherein a pressure of a pressure source for the filling medium in the regulating device is set to a pressure level above the target pressure level.

22. The device according to claim 1, wherein the pressure sensor is arranged in the tracheal tube cuff.

23. The device according to claim 22, wherein the pressure sensor is coupled to the regulating device via a cable.

24. The device according to claim 1, wherein the regulating device comprises an active regulator configured to adjust the pressure level inside the tracheal tube cuff.

25. The device according to claim 24, wherein the active regulator is operated with a fixed timing frequency.

26. The device according to claim 1, wherein a turbulent flow is prevented when moving the filing medium between the regulating device and the tracheal tube cuff.

27. The device according to claim 1, wherein a sealing-pressure-maintaining extracorporeal volume compensation acts in a synchronous manner in the tracheal tube cuff.

28. The device according to claim 1, wherein a thickness of a wall of the tracheal tube cuff is 10 μm.

29. The device according to claim 1, wherein a wall of the tracheal tube cuff is comprised.

30. The device according to claim 1, wherein the tracheal tube cuff consists of polyurethane (PUR) with a material durometer according to Shore of 70 A to 95A.

31. The device according to claim 1, wherein the tracheal tube cuff comprises a multilayer wall structure.

* * * * *